(12) United States Patent
Kaneko et al.

(10) Patent No.: US 10,794,893 B2
(45) Date of Patent: Oct. 6, 2020

(54) METHOD FOR ESTIMATING ABRASION RESISTANCE AND FRACTURE RESISTANCE

(71) Applicant: SUMITOMO RUBBER INDUSTRIES, LTD., Hyogo (JP)

(72) Inventors: Fusae Kaneko, Hyogo (JP); Hiroyuki Kishimoto, Hyogo (JP)

(73) Assignee: SUMITOMO RUBBER INDUSTRIES, LTD., Hyogo (JP)

( * ) Notice: Subject to any disclaimer, the term of this patent is extended or adjusted under 35 U.S.C. 154(b) by 43 days.

(21) Appl. No.: 16/288,751

(22) Filed: Feb. 28, 2019

(65) Prior Publication Data

US 2019/0285609 A1   Sep. 19, 2019

(30) Foreign Application Priority Data

Mar. 14, 2018 (JP) ................. 2018-046850

(51) Int. Cl.
| | | |
|---|---|---|
| G01N 33/44 | (2006.01) | |
| G01N 23/083 | (2018.01) | |
| G01N 23/085 | (2018.01) | |
| G01N 33/00 | (2006.01) | |

(52) U.S. Cl.
CPC ......... *G01N 33/445* (2013.01); *G01N 23/083* (2013.01); *G01N 23/085* (2018.02); *G01N 2033/0003* (2013.01); *G01N 2223/04* (2013.01); *G01N 2223/402* (2013.01); *G01N 2223/615* (2013.01); *G01N 2223/634* (2013.01)

(58) Field of Classification Search
CPC combination set(s) only.
See application file for complete search history.

(56) References Cited

U.S. PATENT DOCUMENTS

2017/0209936 A1*  7/2017  Kanaoka ............... C23C 16/029
2018/0339415 A1*  11/2018  Yoshimura .............. B32B 15/04

FOREIGN PATENT DOCUMENTS

JP        2019078670     *  5/2019  ........... G01N 23/085

OTHER PUBLICATIONS

Awaja et al., "Cracks, microcracks and fracture in polymer structures: Formation, detection, autonomic repair", 2016, Progress in Materials Science 83 (Year: 2016).*

* cited by examiner

*Primary Examiner* — Zhiyu Lu
(74) *Attorney, Agent, or Firm* — Greenblum & Bernstein, P.L.C.

(57) ABSTRACT

Provided is a method for estimating abrasion resistance and fracture resistance by highly accurately analyzing aggregation (dispersion) of sulfur-based materials in polymer composite materials. The present invention relates to a method for estimating abrasion resistance and fracture resistance, the method including: irradiating a polymer composite material containing at least one sulfur-based material selected from the group consisting of sulfur and sulfur compounds with high intensity X-rays; measuring X-ray absorption of a measurement region of the polymer composite material while varying the energy of the X-rays; calculating areas of spots having a high sulfur concentration equal to or greater than a predetermined level in a two-dimensional mapping image of sulfur concentration of the measurement region; and estimating abrasion resistance and fracture resistance based on the areas.

4 Claims, 4 Drawing Sheets
(3 of 4 Drawing Sheet(s) Filed in Color)

METHOD FOR ESTIMATING ABRASION RESISTANCE AND FRACTURE RESISTANCE

TECHNICAL FIELD

The present invention relates to a method for estimating abrasion resistance and fracture resistance.

BACKGROUND ART

In polymer composite materials such as rubber materials, polymer molecules are bridged by sulfur to form cross-linked structures which provide peculiar physical properties such as strength, energy loss due to repeated deformation, and frequency response properties. Such polymer composite materials are essential for applications such as tires and damping materials. However, since for example the expected increase in the demand for tires and other materials in the future may cause shortages of raw materials, there is a need for materials such as rubber materials that can maintain their performance for a long period of time. To this end, it is necessary to improve properties such as abrasion resistance and fracture resistance.

Controlling the cross-linked structure is a key point for improving the abrasion resistance and fracture resistance of rubber materials. For this purpose, it is important to analyze dispersion of sulfur and vulcanization accelerators, for example. Although sulfur mapping techniques based on, for example, X-ray fluorescence analysis (XRF) or energy dispersive X-ray spectrometry (EDX) have been proposed, it is desirable to provide a more accurate method for estimating the abrasion resistance and other properties of materials.

SUMMARY OF INVENTION

Technical Problem

The present invention aims to solve the aforementioned problem and provide a method for estimating abrasion resistance and fracture resistance by highly accurately analyzing aggregation (dispersion) of sulfur-based materials in polymer composite materials.

Solution to Problem

The present invention relates to a method for estimating abrasion resistance and fracture resistance, the method including:

irradiating a polymer composite material containing at least one sulfur-based material selected from the group consisting of sulfur and sulfur compounds with high intensity X-rays;

measuring X-ray absorption of a measurement region of the polymer composite material while varying the energy of the X-rays;

calculating areas of spots having a high sulfur concentration equal to or greater than a predetermined level in a two-dimensional mapping image of sulfur concentration of the measurement region; and estimating abrasion resistance and fracture resistance based on the areas.

Preferably, it is determined that the smaller the area of the largest high sulfur concentration portion consisting of a continuous series of the spots having a high sulfur concentration equal to or greater than a predetermined level, the better the abrasion resistance and fracture resistance.

Preferably, it is determined that the smaller the sum of areas of all high sulfur concentration portions each consisting of a continuous series of the spots having a high sulfur concentration equal to or greater than a predetermined level, the better the abrasion resistance and fracture resistance.

Preferably, the high intensity X-rays are used to measure X-ray absorption at the sulfur K-shell absorption edge in an energy range of 2400 to 3000 eV or X-ray absorption at the sulfur L-shell absorption edge in an energy range of 130 to 280 eV.

Advantageous Effects of Invention

The method according to the present invention includes irradiating a polymer composite material containing at least one sulfur-based material selected from the group consisting of sulfur and sulfur compounds with high intensity X-rays, measuring X-ray absorption of a measurement region of the polymer composite material while varying the energy of the X-rays, calculating areas of spots having a high sulfur concentration equal to or greater than a predetermined level in a two-dimensional mapping image of sulfur concentration of the measurement region, and estimating abrasion resistance and fracture resistance based on the areas. By using this method, it is possible to estimate abrasion resistance and fracture resistance without actually producing products such as tires and testing their durability. Thus, the development time and cost can also be reduced.

BRIEF DESCRIPTION OF DRAWINGS

The patent or application file contains at least one drawing executed in color. Copies of this patent or patent application publication with color drawing(s) will be provided by the Office upon request and payment of the necessary fee.

DESCRIPTION OF EMBODIMENTS

The present invention relates to a method for estimating abrasion resistance and fracture resistance. The method includes: irradiating a polymer composite material containing at least one sulfur-based material selected from the group consisting of sulfur and sulfur compounds with high intensity X-rays; measuring X-ray absorption of a measurement region of the polymer composite material while varying the energy of the X-rays; calculating areas of spots having a high sulfur concentration equal to or greater than a predetermined level in a two-dimensional mapping image of sulfur concentration of the measurement region; and estimating abrasion resistance and fracture resistance based on the areas.

Since controlling the cross-linked structure is a key point for improving abrasion resistance and fracture resistance, it may be contemplated to observe dispersion of vulcanization accelerators in rubber materials by STXM and then estimate abrasion resistance and fracture resistance based on their dispersion size. However, this method may not provide sufficiently accurate estimates because it involves micro area observation, not large-scale observation which is considered actually effective for estimating abrasion resistance and fracture resistance, and also because, although the estimation based on the dispersion size of vulcanization accelerators is considered to correlate to some extent with the cross-linked structure, it does not reflect actual crosslinking data.

In contrast, the present invention provides a method that maps the X-ray absorption, e.g. at the sulfur K-shell absorption edge, on a large scale (large measurement region) to observe variations in sulfur concentration (aggregates of sulfur-based compounds), and estimates the abrasion resistance and fracture resistance of products such as tires based on the areas of spots having a high sulfur concentration equal to or greater than a predetermined level. For example, it may be determined that the smaller the area of the high sulfur concentration portion having the largest area among all the high sulfur concentration portions each consisting of a continuous (linked) series of the spots having a high sulfur concentration (i.e., portions having a high sulfur concentration in which aggregates of sulfur-based compounds and the like are mainly present), e.g., the smaller the largest aggregate size of the sulfur-based compounds, the better the abrasion resistance and fracture resistance.

Accordingly, by subjecting polymer composite materials (specimens) containing sulfur-based compounds such as sulfur or vulcanization accelerators to the method of the present invention, it is possible to estimate the abrasion resistance and fracture resistance of products (e.g. tires) formed from the materials without actually producing such products and testing them for durability.

The polymer composite material to be subjected to the method of the present invention contains at least one sulfur-based material selected from the group consisting of sulfur and sulfur compounds.

The sulfur may be one generally used in the tire industry. Examples include sulfur vulcanizing agents (vulcanizing agents consisting of sulfur, such as powdered sulfur).

Examples of the sulfur compounds include vulcanizing agents other than sulfur such as sulfur-containing vulcanizing agents, e.g. sodium hexamethylene-1,6-bisthiosulfate dihydrate and 1,6-bis(N,N'-dibenzylthiocarbamoyldithio) hexane.

Other examples of the sulfur compounds include vulcanization accelerators (sulfur-containing vulcanization accelerators). Vulcanization accelerators are compounds having a vulcanization accelerating effect which may usually be added (incorporated) and kneaded in a kneading step for rubber compositions. Examples of such vulcanization accelerators include various vulcanization accelerators known in the tire industry, such as guanidine vulcanization accelerators, sulfenamide vulcanization accelerators, thiazole vulcanization accelerators, thiuram vulcanization accelerators, dithiocarbamate vulcanization accelerators, thiourea vulcanization accelerators, and xanthate vulcanization accelerators.

Still other examples of the sulfur compounds include sulfur-containing compounds such as 4,4'-dithiodimorpholine, 2-(4'-morpholinodithio)benzothiazole, and tetramethylthiuramdisulfide.

The polymer composite material preferably includes at least one diene polymer or a rubber blend material or a composite material combining at least one diene polymer or a rubber blend material with at least one resin. Examples of the diene polymer include polymers having double bonds, such as natural rubber (NR), polyisoprene rubber (IR), polybutadiene rubber (BR), styrene butadiene rubber (SBR), acrylonitrile butadiene rubber (NBR), chloroprene rubber (CR), butyl rubber (IIR), halogenated butyl rubber (X-IIR), and styrene isoprene butadiene rubber (SIBR).

Non-limiting examples of the resin include resins generally used in the rubber industry, such as C5 aliphatic petroleum resins, cyclopentadiene petroleum resins, and other petroleum resins.

The polymer composite material may appropriately contain conventional compounding materials known in the rubber field, including, for example, fillers such as carbon black and silica, silane coupling agents, zinc oxide, stearic acid, antioxidants, waxes, and oils. Such a rubber material (rubber composition) may be prepared by known kneading methods, for example. The rubber material may be, for example, a rubber material for tires (rubber composition for tires).

The polymer composite material may be either unvulcanized or vulcanized. It may suitably be a vulcanized composite material because then aggregates with different sizes can be observed which facilitate study of the relationship of the aggregate size with abrasion resistance and fracture resistance.

The present invention includes irradiating a polymer composite material with high intensity X-rays and measuring X-ray absorption of a measurement region of the polymer composite material while varying the energy of the X-rays.

The X-ray absorption may be measured by, for example, X-ray absorption fine structure (XAFS) (e.g. near-edge X-ray absorption fine structure) spectroscopy.

Specifically, for example, the following transmission, fluorescence, and electron yield methods are generally used as methods of irradiating a sample with high intensity X-rays and measuring X-ray absorption while varying the energy of the X-rays.

(Transmission Method)

This method is to detect the intensity of X-rays having transmitted through a sample. For the measurement of the intensity of transmitted light, a photodiode array detector may be used, for example.

(Fluorescence Method)

This method is to detect fluorescent X-rays generated when a sample is irradiated with X-rays. In the detection, a Lytle detector or semiconductor detector may be used, for example. In the transmission method, when the X-ray absorption of an element present in a small amount in a sample is measured, a spectrum with a poor S/B ratio will be obtained because the signal will be small while the background will be high due to the X-ray absorption of elements present in a large amount. In contrast, in the fluorescence method (especially when an energy dispersive detector is used, for example), only the fluorescent X-rays from a target element can be measured, and therefore the elements present in a large amount will have only a small influence. For this reason, this method is effective to measure an X-ray absorption spectrum of an element present in a small amount. Moreover, this method allows detection of fluorescent X-rays generated inside the sample because fluorescent X-rays have high penetrating power (low interaction with substances). Thus, the method is the second most suitable method for obtaining bulk information after the transmission method.

(Electron Yield Method)

This method is to detect a current flowing when a sample is irradiated with X-rays. Thus, the sample needs to be an electrically conductive material. The method also features surface sensitivity (information at a depth of approximately several nanometers below the sample surface). Irradiation of a sample with X-rays causes escape of electrons from elements. Since electrons have a great interaction with substances, their mean free path in a substance is short.

As described above, the transmission method, which is a basic XAFS method that measures X-ray absorption by detecting the intensity of incident light and the intensity of X-rays transmitted through a sample, provides bulk information on the sample, but characteristically has difficulty in measuring compounds, unless they are at concentrations equal to or greater than a predetermined level (e.g., at least several percent by weight). The electron yield method is a surface-sensitive method that provides information at a depth of approximately several tens of nanometers below the sample surface. The fluorescence method is characterized by providing information at some great depth below the surface as compared to the electron yield method, and also by being able to measure compounds even at low concentrations. The fluorescence method is suitable for use in the present invention.

The fluorescence method is then described in greater detail below.

The fluorescence method, which includes monitoring fluorescent X-rays generated when a sample is irradiated with X-rays, indirectly determines X-ray absorption from the intensity of fluorescent X-rays according to the proportional relationship between the amount of X-ray absorption and the intensity of fluorescent X-rays. The fluorescence method is often carried out using an ionization chamber or a semiconductor detector such as a silicon drift detector (SDD) or silicon strip detector (SSD). Although the use of an ionization chamber allows relatively easy measurements, it has difficulty in energy differentiation, and may also increase the background because X-rays scattered from a sample or fluorescent X-rays from elements other than the target element can enter the ionization chamber. Thus, it is necessary to place a solar slit or a filter between the sample and the detector. On the other hand, the use of SDD or SSD allows highly sensitive measurements and energy differentiation, and therefore it is possible to retrieve only the fluorescent X-rays from the target element, thereby providing measurements with good S/B ratios.

The high intensity X-rays preferably have a number of photons of $10^7$ photons/s or more. Such X-rays enable highly accurate measurements. The number of photons of the X-rays is more preferably $10^9$ photons/s or more. The upper limit of the number of photons of the X-rays is not particularly critical, but the X-ray intensity used is preferably low enough not to cause radiation damage.

The high intensity X-rays preferably have a brilliance of $10^{10}$ photons/s/mrad$^2$/mm$^2$/0.1% bw or higher. XAFS spectroscopy requires a continuous X-ray generator as a light source to scan the X-ray energy. Moreover, for detailed analysis of the chemical state, it is necessary to measure an X-ray absorption spectrum with high S/N and S/B ratios. Therefore, most suitable for XAFS measurements are synchrotrons which are continuous X-ray sources and emit X-rays having a brilliance of $10^{10}$ photons/s/mrad$^2$/mm$^2$/0.1% bw or higher, where the "bw" represents the band width of X-rays emitted from the synchrotron. The brilliance of the X-rays is more preferably $10^{11}$ photons/s/mrad$^2$/mm$^2$/0.1% bw or higher. The upper limit of the brilliance of the X-rays is not particularly critical, but the X-ray intensity used is preferably low enough not to cause radiation damage.

Scanning with the high intensity X-rays may suitably be carried out in an energy range of: (1) 2300 to 4000 eV; or (2) 100 to 280 eV. Scanning of these ranges provides measurements of X-ray absorption near the sulfur K-shell and L-shell absorption edges, respectively, thereby obtaining information on the chemical state of sulfur in the material. The energy range (1) is more preferably 2400 to 3000 eV, while the energy range (2) is more preferably 130 to 280 eV.

According to the present invention, the X-ray absorption, e.g. near the sulfur K-shell or L-shell absorption edge, of a measurement region of the polymer composite material may be measured and determined as the sulfur concentration of the measurement region (the amount of sulfur atoms in the measurement region).

Subsequently, the X-ray absorption (sulfur concentration) may be two-dimensionally mapped to create a mapping image which may then be used to observe the distribution of sulfur-based materials (e.g., variations in sulfur concentration, the presence or absence of aggregates of sulfur-based materials) in the image (within the measurement region) to determine spots (whose area depends on the X-ray spot size) having a high sulfur concentration equal to or greater than a predetermined level in the mapping image and calculate their areas. The calculated areas of the spots having a high sulfur concentration equal to or greater than a predetermined level correlate with abrasion resistance and fracture resistance.

Thus, for example, it may be determined that the smaller the area of the largest high sulfur concentration portion or sum of areas of all high sulfur concentration portions each consisting of a continuous series of the spots having a high sulfur concentration equal to or greater than a predetermined level, the better the abrasion resistance and fracture resistance of tires.

As described above, the present invention provides a method that measures an X-ray absorption spectrum of a polymer composite material containing a sulfur-based compound such as sulfur or a sulfur compound by XAFS spectroscopy, creates a two-dimensional mapping image using analysis software such as Igor or Origin to observe the concentration of sulfur (dispersion of sulfur) from the sulfur-based compound in the sample, and then calculates areas of spots having a high sulfur concentration equal to or greater than a predetermined level and estimates abrasion resistance and fracture resistance based on the areas. The following more specifically describes these points.

Figure 1:
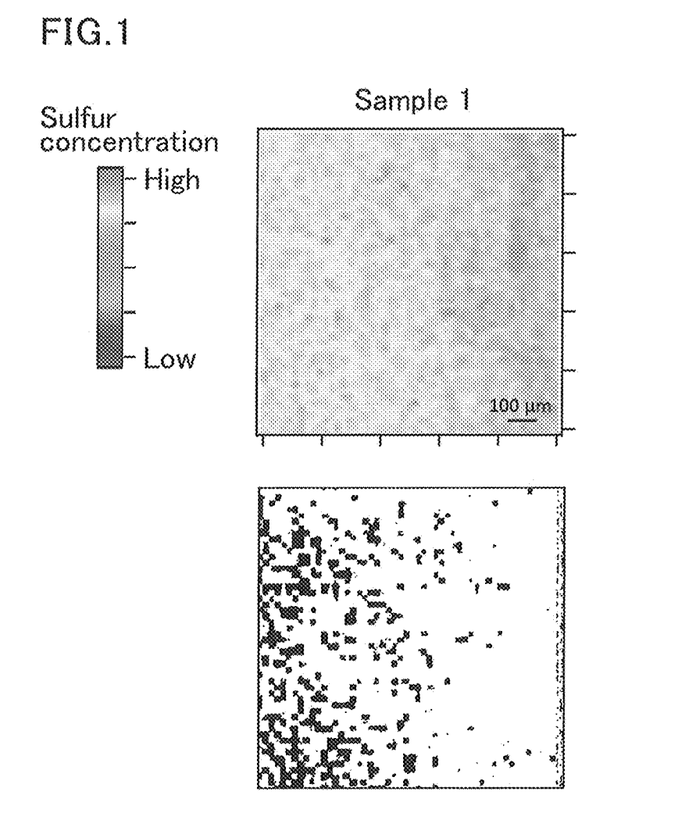
FIG. 1 illustrates examples of a mapping image of sample 1 and a binary image of the mapping image.

FIG. 1 illustrates a mapping image (upper image) of sample 1 (a polymer composite material containing sulfur and vulcanization accelerators) created by mapping the X-ray absorption at the sulfur K-shell absorption edge on a large scale (1 mm$^2$), as well as a binary image (lower image) obtained by binarizing the mapping image using image analysis software such as Image-J to determine the areas of the red spots having a high sulfur concentration in the image. In the mapping image (upper image), the closer to red, the higher the sulfur concentration, while the closer to blue, the lower the sulfur concentration (see the color image submitted). In the binary image (lower image), the black portions indicate spots having a high concentration of sulfur from the sulfur-based compounds in the sample (spots having a high sulfur concentration equal to or greater than a predetermined level).

Figure 2:
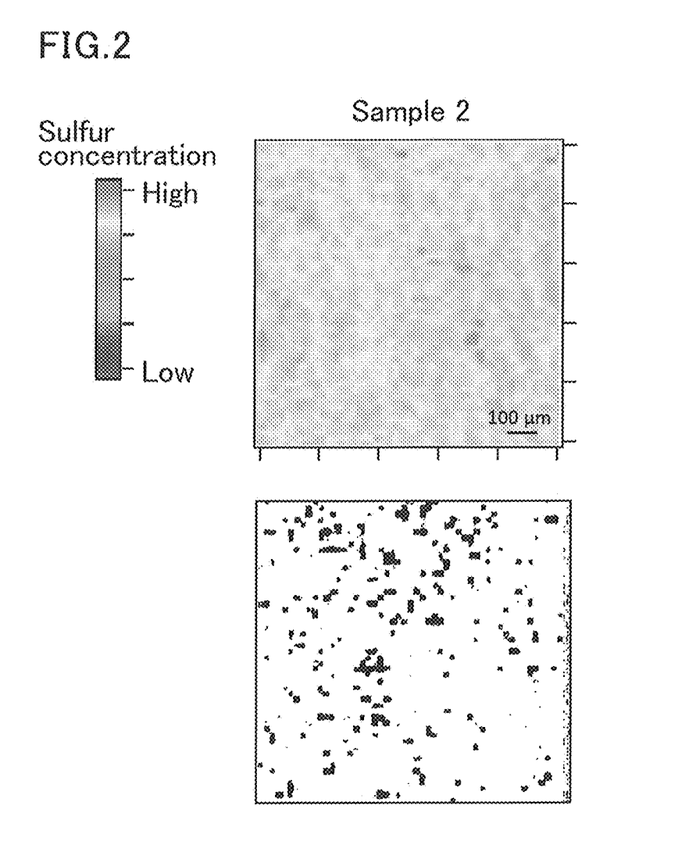
FIG. 2 illustrates examples of a mapping image of sample 2 and a binary image of the mapping image.

FIG. 2 illustrates a mapping image (upper image) and binary image (lower image) similarly created for sample 2 having the same formulation as sample 1 but prepared by a method different from that of sample 1. A comparison between sample 1 of FIG. 1 (upper image) and sample 2 of FIG. 2 (upper image) shows that the number of red spots having a high sulfur concentration (aggregates of sulfur and sulfur compounds) is greater in the image of sample 1.

Figure 3:
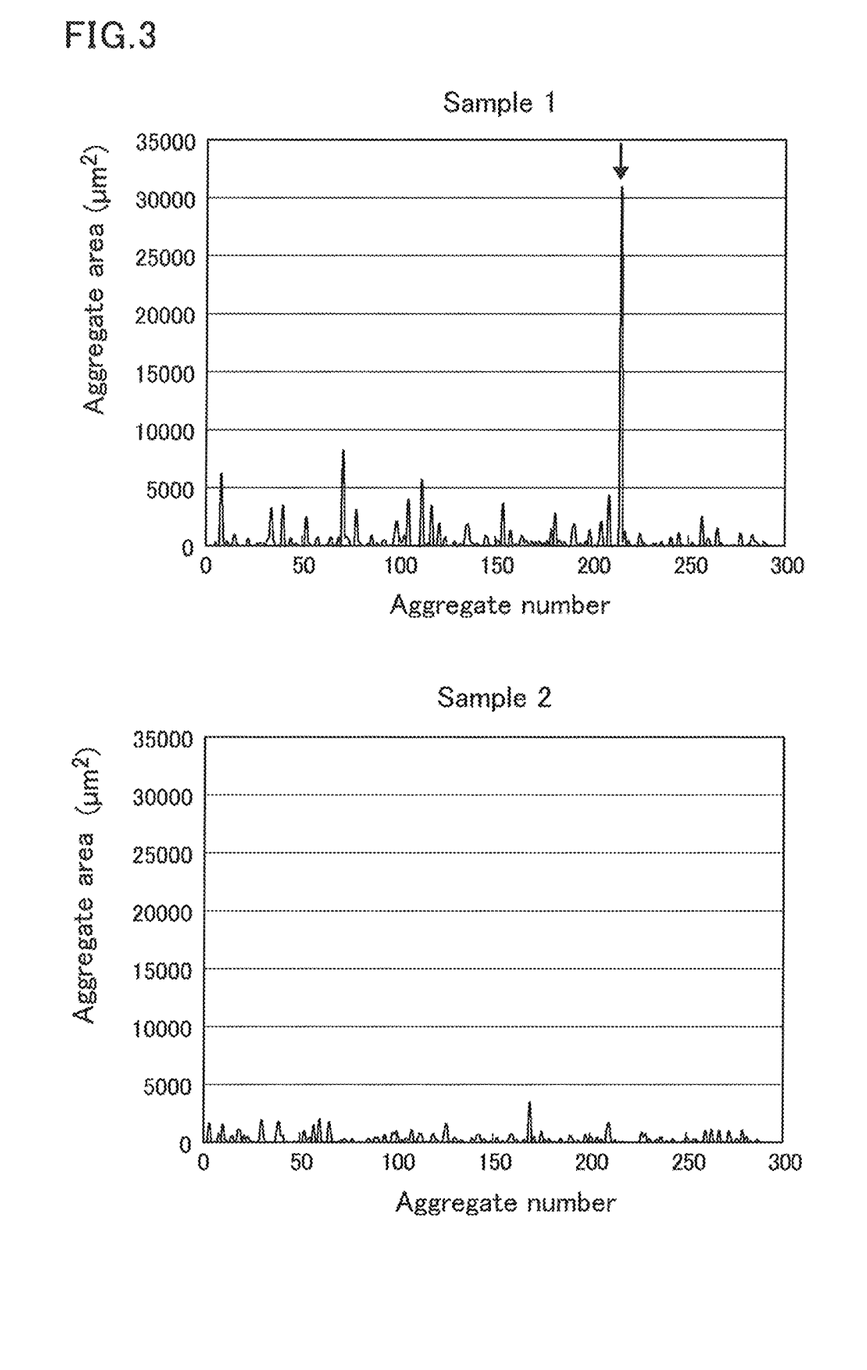
FIG. 3 illustrates exemplary graphs of the relationship between the number of aggregates (aggregate number) and aggregate area of the binary images of the mapping images of FIGS. 1 and 2.
Figure 4:
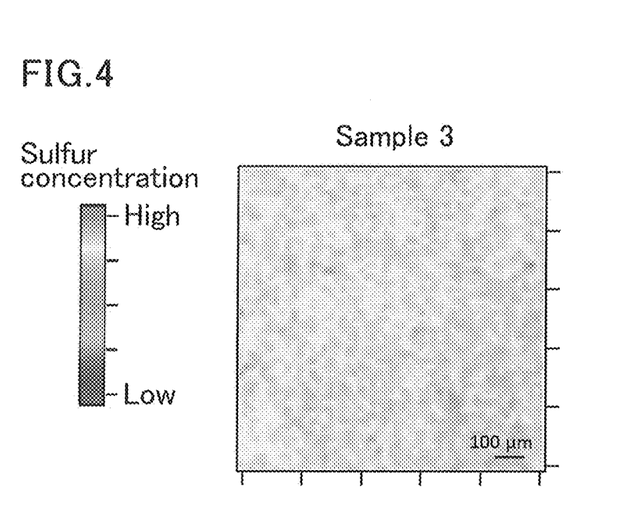
FIG. 4 illustrates an example of a mapping image of sample 3.
Figure 5:
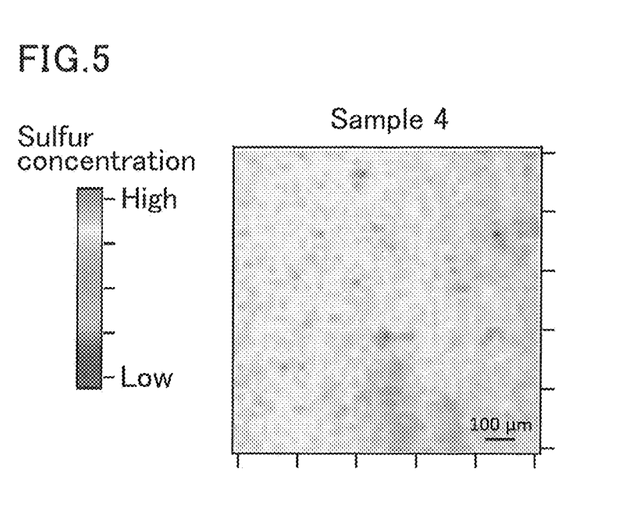
FIG. 5 illustrates an example of a mapping image of sample 4.

FIG. 3 illustrates graphs (upper graph: sample 1, lower graph: sample 2) prepared by calculating the areas of the black portions (high sulfur concentration portions each consisting of a continuous series of the spots having a high sulfur concentration equal to or greater than a predetermined level) in the binary image of FIG. 1 or 2 (lower image) and creating a relationship between the number of aggregates (aggregate number) and aggregate area. The arrow (in the upper graph) indicates that the aggregate area (the aggregate size of the sulfur-based compounds) of the 210th black portion (the 210th aggregate of sulfur-based compounds), among the black portions of sample 1, is about 30000 $\mu m^2$.

Then, the abrasion resistance and fracture resistance of tires formed from each sample can be estimated based on FIG. 3. For example, it may be determined that the smaller the area of the black portion having the largest area among all the black portions (high sulfur concentration portions each consisting of a continuous series of the spots having a high sulfur concentration equal to or greater than a predetermined level) or sum of the areas of all the black portions, the better the abrasion resistance and fracture resistance of tires. Accordingly, since in FIG. 3, the area of the black portion having the largest area among all the black portions of sample 1 is about 30000 $\mu m^2$, whereas that of sample 2 is smaller than 30000 $\mu m^2$, it may be estimated that sample 2 has better properties.

For good abrasion resistance and fracture resistance, the area of the largest black portion (high sulfur concentration portion consisting of a continuous series of the spots having a high sulfur concentration equal to or greater than a predetermined level) is preferably 10000 $\mu m^2$ or smaller, more preferably 8000 $\mu m^2$ or smaller.

In the method of the present invention which includes calculating the areas of the spots having a high sulfur concentration equal to or greater than a predetermined level, the "high sulfur concentration equal to or greater than a predetermined level" may be selected appropriately depending on the compared samples. For example, when it is desired to estimate (compare) the abrasion resistance and fracture resistance of a plurality of samples with high sulfur contents, the sulfur concentration equal to or greater than a predetermined level is set high, and then the areas of the spots having a sulfur concentration equal to or greater than that level are calculated and used for evaluation. On the other hand, in the case of estimation of samples with low sulfur contents in which sulfur disperses relatively well, the sulfur concentration equal to or greater than a predetermined level may be set low to estimate (compare) the properties of the samples.

In the color images of FIGS. 1, 2, 4, and 5, colors are assigned to the pixels (measurement units) depending on the amount (value) of X-ray absorption measured for each pixel according to a preset color scale. The color scale is set so that red corresponds to pixels with an X-ray absorption equal to or greater than a predetermined value, and blue corresponds to pixels with an X-ray absorption equal to or less than a predetermined value. Moreover, as described above, the "high sulfur concentration equal to or greater than a predetermined level" in the present invention may be selected appropriately depending on the compared samples. Accordingly, for example, an appropriate color scale or other settings may be selected for a reference sample, and the same color scale or settings may also be used for a comparative sample, followed by binarization to prepare binary images of the reference sample and the comparative sample which may then be used to compare the properties of both samples.

FIGS. 1 to 3 show examples in which samples are measured on a large scale. In view of evaluation accuracy, the area of the measurement region (the total area measured for X-ray absorption of each sample) is preferably 0.1 $mm^2$ or greater, more preferably 0.5 $mm^2$ or greater. The upper limit of the area is not particularly critical and may be selected appropriately according to the type of device, but it is usually 5 $mm^2$ or smaller. The shape of the measurement region may be selected from any appropriate shape such as a rectangular or circular shape.

X-ray absorption, e.g. at the sulfur K-shell or L-shell absorption edge, is measured for each spot (unit area) in the measurement region and then mapped as the sulfur concentration of the each spot (the amount of sulfur atoms in the each spot). The area of each spot (the unit measurement area depending on the X-ray spot size) is not particularly critical and may be selected appropriately according to the type of device. In view of evaluation accuracy, for example, it is preferably 100 to 2000 $\mu m^2$, more preferably 200 to 1000 $\mu m^2$.

Although FIGS. 1 to 3 show examples in which the sulfur K-shell absorption edge is measured, any method that allows observation on a large scale may be used, and estimation can be made by measuring the sulfur L-shell absorption edge, for example.

Thus, the present invention has been completed based on the finding that there is a relationship between the aggregation of sulfur-based compounds such as sulfur and sulfur compounds (the area of the aggregate of sulfur-based compounds) in a polymer composite material analyzed on a large scale and the abrasion resistance and other properties of products (e.g. tires) formed from the material. The abrasion resistance and fracture resistance of such products can be estimated based on the aggregation (area) observed as described above or by other methods.

EXAMPLES

The present invention is specifically described with reference to, but not limited to, examples below.
<Method for Preparation of Sample>
(Sample 1)
The materials listed in the formulation recipe shown below were kneaded using a roll mill to prepare sample 1 (rubber vulcanizate, vulcanized at 160° C. for 20 min).
(Sample 2)
The materials other than the sulfur and vulcanization accelerators listed in the formulation recipe below were charged into a Banbury mixer to a fill factor of 58% and kneaded at 80 rpm up to 140° C. to give a kneaded mixture. To the kneaded mixture were added the sulfur and vulcanization accelerators according to the formulation recipe to prepare sample 2 (rubber vulcanizate, vulcanized at 160° C. for 20 min).
(Sample 3)
The materials listed in the formulation recipe below were charged into a Banbury mixer to a fill factor of 58% and kneaded at 80 rpm up to 140° C. to prepare sample 3 (rubber vulcanizate, vulcanized at 160° C. for 20 min).

(Sample 4)

The materials other than the sulfur and vulcanization accelerators listed in the formulation recipe below were charged into a Banbury mixer to a fill factor of 50% and kneaded at 80 rpm up to 140° C. to give a kneaded mixture. To the kneaded mixture were added the sulfur and vulcanization accelerators according to the formulation recipe to prepare sample 4 (rubber vulcanizate, vulcanized at 160° C. for 20 min).

(Formulation Recipe)

The formulation is as follows: 50 parts by mass of natural rubber, 50 parts by mass of polybutadiene rubber, 60 parts by mass of carbon black, 5 parts by mass of oil, 2 parts by mass of antioxidant, 2.5 parts by mass of wax, 3 parts by mass of zinc oxide, 2 parts by mass of stearic acid, 1.2 parts by mass of powdered sulfur, 1 part by mass of vulcanization accelerator CZ, and 0.5 parts by mass of vulcanization accelerator DPG.

The materials used are as follows.

Natural rubber: TSR20

Polybutadiene rubber: BR150B available from Ube Industries, Ltd.

Carbon black: SHOBLACK N351 available from Cabot Japan K.K.

Oil: Process X-140 available from Japan Energy Corporation

Antioxidant: NOCRAC 6C (N-1,3-dimethylbutyl-N'-phenyl-p-phenylenediamine) available from Ouchi Shinko Chemical Industrial Co., Ltd.

Wax: OZOACE 0355 available from Nippon Seiro Co., Ltd.

Zinc oxide: Ginrei R available from Toho Zinc Co., Ltd.

Stearic acid: Tsubaki available from NOF Corporation

Powdered sulfur (containing 5% of oil): 5% oil-treated sulfur powder (soluble sulfur containing 5% by mass of oil) available from Tsurumi Chemical Industry Co., Ltd.

Vulcanization accelerator CZ: Nocceler CZ (N-cyclohexyl-2-benzothiazylsulfenamide) available from Ouchi Shinko Chemical Industrial Co., Ltd.

Vulcanization accelerator DPG: Nocceler D (1,3-diphenylguanidine) available from Ouchi Shinko Chemical Industrial Co., Ltd.

(Preparation of Test Tire)

Test tires (size: 195/65R15) containing each of the rubber compositions of samples 1 to 4 in a tread portion were prepared and subjected to tire performance testing as described below.

<Tire Performance Testing>

(Abrasion Resistance)

A vehicle equipped with each set of test tires was run, and the change in the depth of the pattern grooves from before to after 30000 km running was determined. The results are expressed as an index, with the tire of sample 2 set equal to 100. A higher index indicates better abrasion resistance.

(Fracture Resistance)

The tread portion of each test tire was subjected to tensile testing in accordance with JIS K 6251 "Rubber, vulcanized or thermoplastic—Determination of tensile stress-strain properties", and then a fracture parameter defined as TB×EB/2 was calculated. The results are expressed as an index, with the tire of sample 2 set equal to 100. A higher index indicates better fracture resistance.

<Observation of Dispersion of Sulfur and Sulfur Compounds>

(Sampling Method)

Free sulfur was removed from the samples as described in JP 2014-238287 A which is hereby incorporated by reference, and the samples were cut using a microtome to prepare TEM-EDX specimens having a thickness of 100 nm and XAFS specimens having a thickness of 10 µm, which were then mounted on a Cu grid for TEM and a graphite holder, respectively.

Comparative Example

The specimens were subjected to TEM-EDX analysis (commercial device was used).

Example

The specimens were subjected to XAFS spectroscopy near the sulfur K-shell absorption edge under the following conditions to obtain XAFS spectra.

(Device Used)

XAFS: XAFS spectrometer in B-branch of BL27SU at the SPring-8

(Measurement Conditions)

Brilliance: $1 \times 10^{16}$ photons/s/mrad$^2$/mm$^2$/0.1% bw

Number of photons: $5 \times 10^{10}$ photons/s

Monochromator: Si crystal monochromator

Detector: silicon drift detector (SDD)

Measurement method: fluorescence method

Energy range: 2360 to 3500 eV

X-ray spot size: 15 µm×15 µm (each X-ray absorption measurement spot: 20 µm×20 µm)

The sulfur X-ray absorption at 2600 eV of the XAFS spectra of samples 1 to 4 was two-dimensionally mapped (size: 1 mm×1 mm) using Igor to create mapping images as shown in FIGS. 1, 2, 4, and 5. Subsequently, the images were binarized using Image-J to calculate the areas of the black portions (high sulfur concentration portions each consisting of a continuous series of spots having a high sulfur concentration equal to or greater than a predetermined level), which were then used to prepare graphs showing the relationship between the number of aggregates (aggregate number) and aggregate area.

In the binarization, spots where almost only sulfur-based compounds are present are defined as "spots having a high sulfur concentration equal to or greater than a predetermined level" (the area occupied by sulfur-based compounds is about 1 µm$^2$ per µm$^2$ of the spot).

<Evaluation>

In the example (XAFS) and comparative example (TEM-EDX), whether the largest aggregate size of the sulfur-based compounds in the samples was measurable or not was determined. It should be noted that, in the example, the largest aggregate size corresponds to the size of the high sulfur concentration portion having the largest area among all the high sulfur concentration portions each consisting of a continuous series of spots having a high sulfur concentration equal to or greater than a predetermined level in each binary image. Table 1 shows the results.

TABLE 1

| | Sample 1 | Sample 2 | Sample 3 | Sample 4 |
|---|---|---|---|---|
| Example (XAFS) Largest aggregate size (µm$^2$) | 30937 | <8000 | <8000 | 10426 |
| Comparative Example (TEM-EDX) | Not measurable | Not measurable | Not measurable | Not measurable |

TABLE 1-continued

|  | Sample 1 | Sample 2 | Sample 3 | Sample 4 |
| --- | --- | --- | --- | --- |
| Largest aggregate size ($\mu m^2$) |  |  |  |  |
| Abrasion resistance index (Test tire) | 81 | 100 | 101 | 93 |
| Fracture resistance index (Test tire) | 84 | 100 | 104 | 91 |

Table 1 shows that the largest aggregate size of the sulfur-based compounds was not measurable by the TEM-EDX method of the comparative example, whereas it was measurable by the XAFS method of the example. It is also shown that the largest aggregate size (largest area) of the samples determined by the method of the example was correlated with the results of testing for abrasion resistance and fracture resistance of the test tires formed from the samples, i.e., the smaller the largest area, the better the abrasion resistance and fracture resistance.

Thus, it was demonstrated that the method of the present invention makes it possible to analyze aggregation (dispersion) of sulfur-based compounds in materials, e.g. the largest aggregate size of the compounds, and thereby estimate the abrasion resistance and fracture resistance of products formed from the materials.

The invention claimed is:

1. A method for estimating abrasion resistance and fracture resistance, the method comprising:
   irradiating a polymer composite material containing at least one sulfur-based material selected from the group consisting of sulfur and sulfur compounds with high intensity X-rays;
   measuring X-ray absorption of a measurement region of the polymer composite material while varying the energy of the X-rays;
   calculating areas of spots having a high sulfur concentration equal to or greater than a predetermined level in a two-dimensional mapping image of sulfur concentration of the measurement region; and
   estimating abrasion resistance and fracture resistance based on the areas.

2. The method for estimating abrasion resistance and fracture resistance according to claim 1,
   wherein it is determined that the smaller the area of the largest high sulfur concentration portion consisting of a continuous series of the spots having a high sulfur concentration equal to or greater than a predetermined level, the better the abrasion resistance and fracture resistance.

3. The method for estimating abrasion resistance and fracture resistance according to claim 1,
   wherein it is determined that the smaller the sum of areas of all high sulfur concentration portions each consisting of a continuous series of the spots having a high sulfur concentration equal to or greater than a predetermined level, the better the abrasion resistance and fracture resistance.

4. The method for estimating abrasion resistance and fracture resistance according to claim 1,
   wherein the high intensity X-rays are used to measure X-ray absorption at the sulfur K-shell absorption edge in an energy range of 2400 to 3000 eV or X-ray absorption at the sulfur L-shell absorption edge in an energy range of 130 to 280 eV.

* * * * *